United States Patent [19]
Rieger

[11] Patent Number: 5,453,227
[45] Date of Patent: Sep. 26, 1995

[54] PROCESS FOR THE PRODUCTION OF CERAMIC PROSTHESES

[75] Inventor: Wolfhart Rieger, Buch, Switzerland

[73] Assignee: Metoxit AG, Thayngen, Switzerland

[21] Appl. No.: 258,701

[22] Filed: Jun. 13, 1994

[30] Foreign Application Priority Data

Jun. 24, 1993 [CH] Switzerland .......................... 01895/93

[51] Int. Cl.$^6$ .................................................. B29C 31/00
[52] U.S. Cl. ............................. 264/40.1; 264/16; 264/19; 264/66; 264/67
[58] Field of Search ............................. 264/16, 19, 40.1, 264/40.7, 56, 66, 67, 82, 86

[56] References Cited

U.S. PATENT DOCUMENTS 4,626,392  12/1986  Kondo et al. ............................. 264/62
4,842,454  6/1989  Gustavsson et al. ...................... 409/84

*Primary Examiner*—Christopher A. Fiorilla
*Attorney, Agent, or Firm*—Bachman & LaPointe

[57] ABSTRACT

A process for the production of a ceramic prosthesis by forming a blank from a mixture of zirconium oxide and hafnium oxide of between 94.8% and 95.3% by weight, yttrium oxide of between 4% and 5.2% by weight, and any further oxide as a balance of less than 1% by weight, with a monoclinic proportion of below 5% by volume. The blank is put into the shape of the required prosthesis by means of a rotating tool of metallically bound diamond grains, using specific operating parameters for the tool.

6 Claims, No Drawings

PROCESS FOR THE PRODUCTION OF CERAMIC PROSTHESES

BACKGROUND OF THE INVENTION

Prostheses, whether in the form of endoprostheses or exoprostheses, can be produced from metallic and ceramic materials, using processing procedures which are specifically matched to those materials. The production of prostheses of a complicated configuration, with a high level of precision in terms of shape, dimensions and fit predominantly involves the use of metal in conjunction with machining procedures which are known from metal machining. Titanium with its alloys and chromium-cobalt steels have proved to be successful for metallic prostheses. The advantage of using metals of the specified kind is due to the fact that prostheses can be produced by machine with very close tolerances in regard to precision in respect of shape, dimensions and fit. However metals suffer from the disadvantage that their properties are not entirely satisfactory for endoprostheses and exoprostheses. Chromium-cobalt steels are distinguished by having high levels of strength but they are on the other hand susceptible to fluctuations in the pH-value of body fluids. The situation is precisely the reverse in the case of titanium alloys.

While the use of ceramic materials for prostheses makes it possible to achieve high levels of strength and a high degree of chemical resistance, the production of ceramic pros theses on the other hand involves considerably greater difficulties than the production of metallic prostheses so that the use of ceramic materials has been generally limited to load-bearing prostheses of an uncomplicated shape, such as ball joints, without matching contouring operations using simple machining procedures after dense sintering, such as ball grinding and polishing. The area of high-precision ceramic prostheses which are of a complex three-dimensional shape and which are also shaped individually for a patient, for example finger, knee and vertebral prostheses, is largely closed to ceramic prostheses. That is due to the need for subjecting pros theses to an unavoidable dense sintering or infiltration operation so that the prostheses are chemically resistant, while enjoying high strength values, and also assume further properties which they do not enjoy in the porous and therefore non-sintered condition. Dense sintering or infiltration alters dimensions and contours when preproduced in a porous condition, so that after the sintering operation the prosthesis has to be subjected to a further working operation in order to restore the prosthesis to the required precision in terms of shape and dimensions. That further working operation is a very difficult one due to the level of hardness of the prosthesis after the sintering or infiltration operation. Added to that is the fact that ceramic prosthesis materials are required to have properties which are not encountered in all ceramics but only a few thereof, in relatively narrow ranges of composition. Endoprostheses such as for example finger, knee and vertebral prostheses and the like of ceramic materials, and it is to endoprostheses of that kind that the invention is also directed besides comparable exoprostheses apart from those in the mouth region, can only be used as prostheses when their material is physiologically completely harmless, the ceramic therefore being bioinert and thus resistant to body fluids, and biocompatible. Further requirements, to prevent the absorption of body fluids, is good dense sinterability, and in the densely sintered condition a high level of strength and a high degree of resistance to abrasion wear. Ceramic materials have to meet those requirements overall, as otherwise they cannot be considered for ceramic prostheses in both of the areas referred to above.

For larger load-bearing endo- and exoprostheses, for example ball joints, two ceramic materials have proven themselves to be suitable, more specifically aluminum oxide ($Al_2O_3$) with an $Al_2O_3$ proportion of 99.85%, with the balance being other constituents, and zirconium oxide ($ZrO_2$) of predominantly tetragonal structure, stabilized by magnesium oxide ($MgO_2$) or by an oxide of the rare earths, preferably yttrium oxide ($Y_2O_3$) or cerium oxide ($CeO_2$). The above-mentioned ceramic materials are thought not to be suitable for small or very small prostheses of a complicated configuration and involving a very high level of accuracy in terms of dimensions and shape, as a result of the dense sintering operation with the subsequent machining difficulties resulting therefrom, so that metals dominate for production of prostheses of the above-indicated kind.

SUMMARY OF THE INVENTION

An object of the present invention is to provide a process for the production of ceramic pros theses with which it is possible to produce ceramic prostheses involving the same variety in respect of contour and accuracy in respect of shape, dimensions and fit as metallic prostheses.

Another object of the present invention is to provide a process for the production of ceramic prostheses which by virtue of the operating procedure involved can at least extensively satisfy the requirements made in respect of endo- and exoprostheses.

Still another object of the present invention is to provide a process for the production of ceramic prostheses which involves using materials of specific compositions and working steps employing specific parameters to produce prostheses enjoying a high degree of accuracy.

In accordance with the principles of the present invention the foregoing and other objects are attained by a process for the production of ceramic prostheses comprising forming or shaping a blank from, in percent by weight, zirconium oxide ($ZrO_2$) and hafnium oxide ($HfO_2$), of between about 94.8% and 95.3%, yttrium oxide ($Y_2O_3$) of between about 4% and 5.2%, and further oxides as a balance of less than about 0.1%, with a monoclinic proportion of below about 5% by volume. The blank is subjected to a working-over operation to form a prosthesis, by means of a rotating tool comprising metallically bound diamond grains, at a speed of rotation of between about 10,000 and 50,000 revolutions per minute, at infeed rates (that is to say towards the blank to remove material therefrom) of between about 0.1 and 0.7 millimeters per minute, feed rates, that is to say along the workpiece, of between about 0.3 and 3.0 centimeters per second, and with surface speeds for the tool of between about 0.5 and 9.0 meters per second.

DETAILED DESCRIPTION OF PREFERRED EMBODIMENTS

It was surprisingly found that with the operating procedures of the process in accordance with the invention, it is possible to produce densely sintered ceramic prostheses, that is to say which in accordance with the invention comprise for example a zirconium oxide, enjoying the same accuracy in regard to shape and dimensions as metallic prostheses. By virtue of the high level of hardness of the densely sintered ceramic, it was not to be expected that the required levels of accuracy in terms of shape and dimensions could be achieved with the process parameters in accordance with the invention. The for example zirconium oxide in accordance with the invention is bioinert and biocompatible and thus satisfies all further requirements to be made in respect of ceramic prosthesis materials, so that the present invention makes it possible to gain entry with ceramic materials into the part of prosthetics which hitherto was predominantly reserved for metals as prosthesis materials, with the advantages deriving therefrom.

In accordance with the invention, for the purposes of producing a prosthesis, the procedure can start from a densely sintered or infiltrated semimanufactured article, for example a round blank or disk of zirconium oxide, by the prosthesis being machined out of the semi-manufactured article in accordance with a pattern, although zirconium oxide in the densely sintered state is substantially more difficult to machine than aluminum oxide so that aluminum oxide would tend to present itself for prosthetic purposes in this area. In an alternative procedure the process can initially start from a porous blank, whereafter the blank is subjected to a working operation to afford a prosthesis, under dimensional control, the porous prosthesis then being subjected to dense sintering or infiltration with dimensional control to constitute an intermediate product, whereupon finally the intermediate product is machined to afford the final shape and dimensions by means of the operating procedure according to the invention.

It is also in accordance with the invention to produce a ceramic prosthesis blank member by means of a mold and slip casting, whereupon the blank member is dried, roasted or fired, subjected to hot isostatic post-compacting and then subjected to oxidizing post-treatment. The shaped blank corresponding to the prosthesis can then be subjected to finishing machining in accordance with the invention.

EXAMPLES

The invention will be described in greater detail hereinafter by means of Examples.

Example I: Finger Joint

A plastic model of an insert for a finger joint (proximal phalanx) is measured by means of a 3D-measuring machine and the measurement data are read into a control apparatus for processing the measurement data. A blank in the form of a plate of dimensions 20×10×32 mm is produced from a material of the composition $ZrO_2$-TZP with a $ZrO_2$-$HfO_2$-proportion of between 94.8 and 95.3% by weight, with a $Y_2O_3$ content of between 4.8 and 5.2% by weight, and a maximum concentration of further oxides (impurities) of less than 0.1% with demonstrated biocompatibility, with a menoclinic proportion of below 5% by volume, and a radioactivity level of less than 10 Bq per kg, corresponding to a maximum of 0.03 microsievert/year of radiation loading. The shape of the proximal phalanx is ground out of that plate, using a machining apparatus which is controlled in three directions by the control apparatus. For that purpose the machining apparatus uses tools comprising metallically bound diamond grains, which are 6 mm in diameter. The selected speed of tool rotation is 22,000 rpm while the surface speed is 0.69 meter per second. The infeed rate, that is to say the rate of feed of the tool towards the blank to be ground and thus the rate of blank material removal is 0.2 millimeters per minute while the tool feed rate, that is to say the rate of feed along the blank, is 0.7 centimeter per second.

After the termination of the machining operation the implant is polished to a roughness depth of better than Ra=0.08 μm in the region of the joint face by multi-stage polishing.

Example II: Middle Phalanx

A plastic model of an insert for a finger joint (middle phalanx) is measured by means of a 3D-measuring machine and the measurement data are read into a control apparatus for processing same. A blank in the form of a plate measuring 15×10×28 mm is produced from a material of the composition $ZrO_2$-TZP with a $ZrO_2HfO_2$-proportion of between 94.5 and 95.3% by weight, a $Y_2O_3$ content of between 4.8 and 5.2% by weight and with a maximum concentration of further oxides (impurities) of less than 0.1%, with proven biocompatibility and with a monoclinic proportion of below 5% by volume and a radioactivity level of less than 10 Bq per kg corresponding to a maximum of 0.03 microsievert/year of radiation loading. The shape of the middle phalanx is ground out of that plate using a machining apparatus controlled in three directions by the control apparatus. The grinding operation is effected using tools comprising metallically bound diamond grains, being of a diameter of 5 mm. The selected speed of tool rotation is 28,000 revolutions per minute, the surface speed is 0.73 meter per second, the infeed rate is 0.3 millimeter per minute and the feed rate along the workpiece is 0.85 centimeter per second. After termination of the machining operation the sliding surface of the implant is brought to a roughness depth of better than 0.05 μm.

Example III: Knee Joint

A plaster mold or cast is made from a three-dimensional metal model, which is enlarged linearly by 30%, of a left femoral knee joint portion. That mold is then used to produce a ceramic blank member by a suitable shaping procedure such as slip casting or an equivalent process. The composition of the raw material used for the blank is: $ZrO_2$+ $HfO_2$= 94.9% by weight; $Y_2O_3$= 5.02% by weight; and impurities=0.08%. The ceramic blank is dried and roasted at 1465° C. After the roasting operation it is subjected to a hot isostatic post-compacting operation treatment, which is referred to as a HIP-treatment, at a pressure of 900 bars, at a temperature T=1375° C., for a period of 1 hour, in an argon atmosphere. The material is then subjected to an oxidizing post-treatment for 1 hour at 1100° C. The resulting white ceramic is distinguished by proven biocompatibility, a monoclinic proportion of below 5% by volume and a radioactivity level of less than 10 Bq per kg, corresponding to a radiation loading of a maximum of 0.03 microsievert per year (averaged over 50 years).

The blank measuring 82.6×66.4×63.5 mm is fixed in a rectangular holder by means of a suitable receiving means. The external shape of the femoral knee joint is machined by means of a machining apparatus in two stages of CIM (Computer Integrated Manufacturing). That operation is effected using metal-bound diamond tools (grinding points) of diameters of 12 and 14.5 mm with a hollow structure and a hard metal or carbide holding means. The selected grain size is stepped from D91 through D126 to D151.

The speed of tool rotation is 45,000 rpm, the surface speed for the tool is 2.8 meters per second, the infeed rate towards the blank is 0.4 mm per minute and the advance rate along the blank is 0.8 centimeter per second.

The articulated joint surfaces are then contour-matched by means of a vibrating polishing stage and diamond pastes to polish them to a surface quality of better than 0.09 μm (Ra).

Example IV: Cervical Vertebra Stabilizer

A plate measuring 18×26–94 mm and of a thickness of 0.5–1.5 mm is axially pressed by means of a suitable pressing tool from ZrO$_2$-TZP material of the composition set forth in Example III. In the longitudinal direction the plate has a cylindrical curvature corresponding to a radius of between 50 and 250 mm, preferably 150 mm.

The blanks of that kind are roasted or fired in an oxidizing atmosphere under conditions as set forth in Examples I through III. After the sintering operation the plate is gripped in a holder by means of a suitable receiving means thereof and machined in accordance with a previously input ted program of 3D CIM ( Three-dimensional Computer Integrated Manufacturing). In that procedure the external contours are machined by means of diamond milling cutters and the inner openings are machined by boring or milling by means of suitable diamond tools. The diamond cutters or tools comprise metallically bound diamond grains. The machining conditions are as follows:

—tool diameter 4 mm
—speed of tool rotation 50,000 rpm
—surface speed 8.3 meters per second
—diamond grain size D126
—feed rate along the blank 1.5 centimeters per second
—infeed rate 0.6 millimeter per minute.

After machining of the contours the workpiece is subjected to a surface smoothing operation by sliding grinding, the grinding bodies comprising 92% Al$_2$O$_3$. The surface quality which can be achieved is Ra =0.86 μm.

It will be appreciated that the above-described processes for the production of ceramic prostheses have been set forth solely by way of example and illustration of the principles of the present invention and that various modifications and alterations may be made therein without thereby departing from the spirit and scope of the invention.

What is claimed is:

1. A process for the production of a ceramic prosthesis comprising:

(a) forming a blank from a mixture of zirconium oxide (ZrO$_2$) and hafnium oxide (HfO$_2$) of between 94.8% and 95.3% by weight, yttrium oxide (Y$_2$O$_3$) of between 4% and 5.2% by weight, and any further oxide as a balance of less than 0.1% by weight, wherein percentages by weight are based on the total weight of the blank, with a monoclinic proportion of below 5% by volume, and (b) working over the blank to form a prosthesis by means of a rotating tool comprising metallically bound diamond grains at a speed of rotation of between 10,000 and 50,000 revolutions per minute, at an infeed rate of between 0.1 and 0.7 millimeters per minute, a feed rate along the workpiece of between 0.3 and 3.0 centimeters per second, and with a surface speed for the tool of between 0.5 and 9.0 meters per second.

2. A process as set forth in claim 1 wherein the blank is subjected to dense sintering.

3. A process as set forth in claim 1 wherein the blank is preshaped in a porous condition in accordance with the prosthesis and then subjected to dense sintering.

4. A process as set forth in claim 1 wherein the blank is subjected to infiltration.

5. A process asset forth in claim 1 wherein the blank is formed as a prosthesis blank member by slip casting, dried, roasted, subjected to hot isostatic post-compacting and then subjected to oxidizing post-treatment.

6. A process as set forth in claim 1 wherein the working-over operation is effected by means of digital detection and calculation of the dimensions of a prosthesis pattern, input of the detection and calculation data into a data-processing control means and output of the data to a machining means movable in three co-ordinates for moving said tool.

\* \* \* \* \*